United States Patent
König et al.

(10) Patent No.: US 6,365,611 B1
(45) Date of Patent: Apr. 2, 2002

(54) PENTAERYTHRITE DERIVATIVES, THE PRODUCTION AND USE THEREOF AND INTERMEDIATE PRODUCTS FOR THE SYNTHESIS OF THE SAME

(75) Inventors: Gerd König, Zwickau; Ulrich Hess, Berlin; Anne-Katrin Windeck, Berlin; Holger Brosig, Berlin, all of (DE)

(73) Assignee: ISIS PHARMA GmbH, Zwickau (DE)

( * ) Notice: Subject to any disclaimer, the term of this patent is extended or adjusted under 35 U.S.C. 154(b) by 0 days.

(21) Appl. No.: 09/445,782

(22) PCT Filed: Jun. 11, 1998

(86) PCT No.: PCT/DE98/01635
§ 371 Date: Feb. 29, 2000
§ 102(e) Date: Feb. 29, 2000

(87) PCT Pub. No.: WO98/56759
PCT Pub. Date: Dec. 17, 1998

(30) Foreign Application Priority Data

Jun. 11, 1997 (DE) .......................... 197 25 340

(51) Int. Cl.[7] ..................... C07D 271/07; C07C 229/22; A61K 31/41
(52) U.S. Cl. ................. 514/364; 514/534; 514/568; 548/132; 560/169; 562/564
(58) Field of Search .............. 548/132; 560/169; 562/564; 514/364, 534, 568

(56) References Cited

U.S. PATENT DOCUMENTS 5,037,849 A  8/1991  Simon et al. ............... 514/509
5,859,053 A  1/1999  Lesur et al. ............... 514/509

FOREIGN PATENT DOCUMENTS

FR         6.487 M       1/1998
WO     WO 98/15521       4/1998 ......... C07C/203/04

OTHER PUBLICATIONS

Hewlins et al., "Nitration of α,β–unsaturated esters. Evidence for positive charge build–up adjacent to carbonyl carbon," *J. Chem., Soc., Perkin Trans. 1* (1997) (10), 1559–1570.

*Primary Examiner*—Robert Gerstl
(74) *Attorney, Agent, or Firm*—Marshall, Gerstein & Borun

(57) ABSTRACT

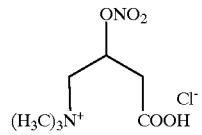

(XII)

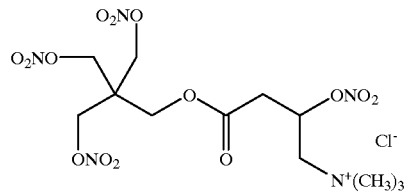

(XVI)

The invention relates to novel compounds derived from pentaerythrite compounds of formula (XII) and (XVI), which can be used as pharmaceutically active substances, specially in the treatment of cardiac and circulatory diseases.

8 Claims, No Drawings

PENTAERYTHRITE DERIVATIVES, THE PRODUCTION AND USE THEREOF AND INTERMEDIATE PRODUCTS FOR THE SYNTHESIS OF THE SAME

This application is a 371 of PCT/DE98/01635 filed Jun. 11, 1998.

SCOPE OF THE INVENTION

The invention presented here relates to new pentaerythritol derivatives, their preparation and use and intermediates for synthesis of the same, which are used in particular as pharmaceutical products.

KNOWN TECHNICAL BACKGROUND

Organic nitrates such as glycerol trinitrate (GTN) (Murrel, Lancet: 80, 113, 151 (1879)), pentaerythrityl tetranitrate (PETN) (Risemann et al., Circulation, Vol. XVII, 22 (1958), U.S. Pat. No. 2,370,437), isosorbitol-5-mononitrate (ISMN) (DE-OS-22 21 080, DE-OS-27 51 934, DE-OS-30 28 873, DE-PS-29 03 927, DE-OS-31 02 947, DE-OS-31 24 410, EP-A1-045 076, EP-A1-057 847, EP-A1-059 664, EP-A1-064 194, EP-A1-067 964, EP-A1-143 507, U.S. Pat. Nos. 3,886,186, 4,065,488, 4,417,065, 4,431,829), isosorbitol dinitrate (ISDN) (L. Goldberg, Acta Physiolog. Scand. 15, 173 (1948)), propatyl nitrate (Médard, Mem. Poudres 35: 113 (1953)), trolnitrate (FR-PS-984 523) or nicorandil (U.S. Pat. No. 4,200,640) and similar compounds are vasodilators, some of which have been used for many decades for the selective treatment of angina pectoris and ischaemic heart disease (IHK) with a very wide therapeutic application (Nitrangin®, Pentalong®, Monolong®, etc.). Other pentaerythrityl nitrates and their preparation have also been described (Simecek, Coll. Czech. Chem. Comm. 27 (1962), 363; Camp et al., J. Am. Chem. Soc. 77 (1955), 751). Organic nitrates of a more recent type such as for example SPM 3672 the ethyl ester of (N-[3-nitratopivaloyl]-L-cysteine) (U.S. Pat. No. 5,284,872) and its derivatives are intended to have comparable and improved pharmacological efficacy when used in the areas mentioned above. Furthermore, the preparation of 3-nitryloxy-2,2-bis-(nitryloxymethyl)propionic acid and its methyl ester (Nec. Chem. Prum. (1978), 28 (2), 84) has also been disclosed. The galenic processing of organic nitrates to give pharmaceutical preparations for the treatment of angina pectoris or ischaemic heart disease is generally well recognised. It is performed using methods of operation and rules which are generally familiar to a person skilled in the pharmaceutical field, wherein the choice of technologies to be used and the galenic auxiliary agents to be used are governed in the first instance by the active substance to be processed. In this case questions relating to its chemicophysical properties, in particular the explosive properties which are known to be associated with organic nitrates, which requires the use of special safety precautions and special processing technologies, the form of application chosen, the period of activity required and the avoidance of medicament/auxiliary agent incompatibilities are of particular importance. When using medicaments for angina pectoris or ischaemic heart disease, peroral, parenteral, sublingual or transdermal application in the form of tablets, dragees, capsules, solutions, sprays or patches has been described in particular (DD-A5-293 492, DE-AS-26 23 800, DE-OS-33 25 652, DE-OS-33 28 094, DE-PS-40 07 705, DE-OS-40 38 203, JP application 59/10513 (1982)). In addition to use as a nitrosing substance which has been disclosed for many years, their use for the treatment and prevention of illnesses which are caused by pathologically elevated concentrations of sulfur-containing amino acids in the body fluids has also been described. These conditions, caused by congenital or acquired defects in the metabolism of these amino acids and which are characterised by elevated blood and urine concentrations of said amino acids (homocystinurea), are combined under the expression homocystinanaemia (WO-A1-92/18002). The use of specific organic nitrates as endothelial protective agents (DE-A1-44 10 997) and as agents for the treatment of erectile disfunction (WO-A1-96/32118) has been described recently. Furthermore, it is known that 3-amino-1,2,4-oxadiazol-5-ones are suitable as proactive drugs for hydroxyguanidines (Rehse et al. Arch. Pharm. Pharm. Med. Chem. 329, 535 (1996)). On the one hand, the currently disclosed organic nitrates (esters of nitric acid) are associated with a number of therapeutic disadvantages. Thus, for instance, so-called nitrate tolerance is observed; i.e. the decrease in the effect of nitrate at high dosage or when administering nitrates with a long-term effect. Side effects such as headaches, nausea, dizziness, feeling weak, reddening of the skin and the risk of a large drop in blood pressure with reflectorial tachycardia have also been demonstrated (Mutschler, Arzneimittelwirkungen, Wissenschaftliche Verlagsgesellschaft mbH, Stuttgart, 1991). On the other hand, PETN has a number of outstanding properties as an active substance which is the reason for the preferred use of this compound as a pharmaceutical product as compared with other organic nitrates, wherein however restricted bioavailability of this active substance has been observed (set of monographs "Pentaerythrityltetranitrat" Dr. Dietrich Steinkopff Verlag, Darmstadt, 1994 to 1995). Lipophilic organic nitrates are generally active for only a short time due to a relatively rapid metabolic degradation to give less active or inactive biotransformation products (Bonn, "Pharmakokinetik organischer Nitrate" in "Pentaerythrityltetranitrat", Dr. Dietrich Steinkopff Verlag, Darmstadt, 1995).

DESCRIPTION OF THE INVENTION

The object of the invention is to provide new compounds derived from pentaerythritol with pharmacologically advantageous effects.

The object of the invention is achieved by the new compounds of the formulae (I) and (III)

wherein $R^1$ represents a group of the formula (II), (II)

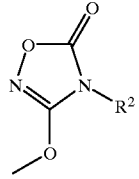

and $R^3$ represents a group of the formula (IV)

(IV)

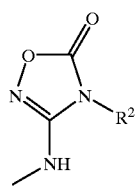

$R^2$ represents a $C_1$ to $C_{20}$ alkyl group, in particular methyl, ethyl, n-propyl, i-propyl, n-butyl, n-pentyl, n-hexyl, n-octyl, benzyl, cyclohexylmethyl, 4-chlorobenzyl, 4-nitrobenzyl, 2-phenylethyl, 3-phenylpropyl, 3-cyclohexylpropyl, 3-phthalimidylpropyl, 1-naphthylmethyl, cinnamyl, 5-ethoxycarbonylbutyl, 3-aminopropyl, —(CH$_2$)$_3$CH(NHCOCH$_3$)COOH, —(CH$_2$)$_3$CH(NHCOCH$_3$)COOCH$_3$, or 1,6-hexane-bis and m to p are integers, for which the following is true: m+n+o+p=4, m≧1 and o and/or p≧1. Compounds in which R$^2$ represents n-butyl, n-pentyl, n-hexyl, benzyl, 2-phenylether, 3-phenylpropyl, 3-phthalimidylpropyl or 5-ethyoxycarbonylbutyl are preferred.

The starting compounds for synthesising compounds of the formulae (I) and (III) are pentaerythritol or its nitrates, i.e. pentaerythrityl mononitrate (PEMN), pentaerythrityl dinitrate (PEDN), pentaerythyrityl trinitrate (PETriN) and pentaerythrityl tetranitrate (PETN), which are synthetically available in good yields in a manner known per se (Simecek, Coll. Czech. Chem. Comm. 27 (1962), 363; Camp et al., J. Am. Chem. Soc. 77 (1955), 751). The compounds PEMN, PEDN and PETriN are converted into the corresponding tri-, di- or monocarboxylic acids by complete or partial oxidation of any hydroxymethyl groups present, and the corresponding derivatives with nitroxy, hydroxyl and carboxyl functions are optionally obtained from these by partial hydrazinolysis of the corresponding nitrate function. The formation of compounds of the formulae (I) and (III) is performed by methods of synthesis and procedures which are familiar to a person skilled in the art, for example by known ester or amide-forming reactions. Compounds of the formula (IV.1), (FIG. 1), are used as starting materials which are also required and the synthesis of these is described in Rehse et al; Arch. Pharm. Pharm. Med. Chem 329, 535 (1996), wherein reference is now made to the disclosures in this publication, and in which in addition one or two hydrogen atoms in the amino group may be replaced by a suitable leaving group, and also compounds of the formula (V),

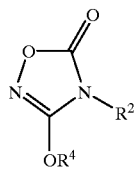

(V)

in which R$^2$ is defined in the same way as for formula (I) and R$^4$ represents H or a suitable leaving group, which are obtainable in good yield from compounds of the formula (IV.1) via the reaction scheme shown in FIG. 1.

FIG. 1

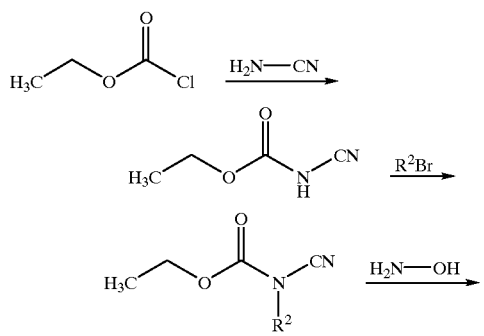

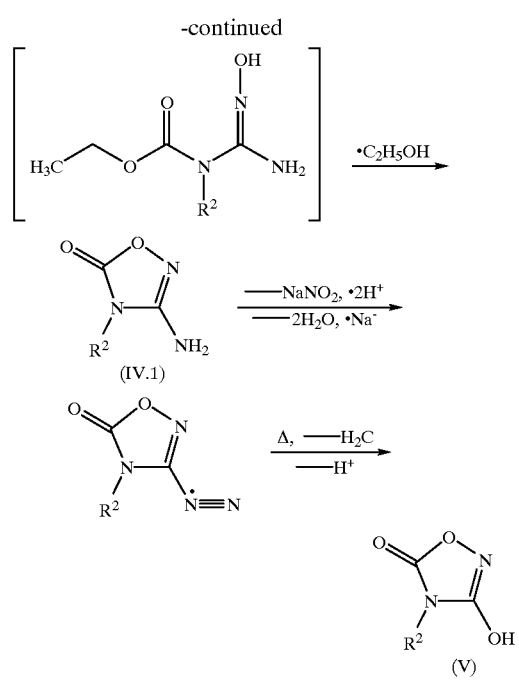

Compounds of the formula (V)

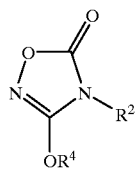

(V)

in which R$^2$ is defined in the same way as given for formula (I) and R$^4$ represents H, a C$_1$ to C$_6$ alkanoyl group, salicyloyl or acetylsalicyloyl, are independent embodiments of the invention. Compounds in which R$^2$ represents n-butyl, n-pentyl, n-hexyl, benzyl, 2-phenylethyl, 3-phenylpropyl, 3-phthalimidylpropyl or 5-ethoxycarbonylbutyl are preferred. Furthermore, compounds in which R$^4$ represents salicyloyl or acetylsalicyloyl and compounds in which R$^2$ represents n-butyl, n-pentyl, n-hexyl, benzyl, 2-phenylethyl, 3-phenylpropyl, 3-phthalimidylpropyl or 5-ethoxycarbonylbutyl and R$^4$ represents salicyloyl or acetylsalicyloyl are also preferred.

Compounds of the formula (VI) may also be used to achieve the object of the invention,

(VI)

in which R$^5$ is (2-carboxyphenyl)oxy or (2-alkoxycarbonylphenyl)oxy and m to p are integers, and: m+n+o+p=4, m≧1 and o and/or p≧1, furthermore compounds of the formula (VII),

(VII)

in which R$^6$ is salicyloyl or acetylsalicyloyl and q to s are integers, and:

q+r+s=4 and r and s are ≧1, furthermore compounds of the formula (VIII),

(VIII)

in which $R^7$ is a group of the formula (IX)

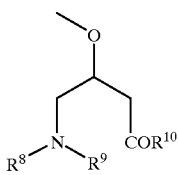
(IX)

$R^8$ and $R^9$, independently, represent a $C_1$ to $C_6$ alkyl group or together represent a $C_1$ to $C_6$ alkylene group, $R^{10}$ represents OH, $NHR^8R^9$, $C_1$ to $C_6$ alkoxy, (2-carboxyphenyl)oxy, (2-alkoxycarbonylphenyl)oxy, (1-carboxymethyl-2-dialkylamino)ethoxy, (1-carboxymethyl-2-trialkylammonium)ethoxy, (1-alkoxycarbonylmethyl-2-dialkylamino)ethoxy, (1-alkoxycarbonylmethyl-2-trialkylammonium)ethoxy, and m to p are integers, and:

$$m+n+o+p=4, m \geq 1 \text{ and } o \text{ and/or } p \geq 1.$$

A particular embodiment of the present invention is compounds of the formula (X),

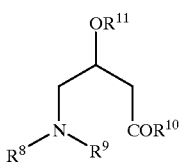
(X)

in which $R^8$ to $R^{10}$ are defined in the same way as for formula (IX) and $R^{11}$ represents $NO_2$, and compounds of the formula (XI) derived therefrom

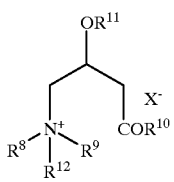
(XI)

in which $R^{12}$ also represents a $C_1$ to $C_6$ alkyl, in particular methyl, ethyl or n-propyl group, and X represents a group capable of forming an anion, which does not have to be present if the group $COR^{10}$ has the ability to form internal salts. Compounds of the formula (XII)

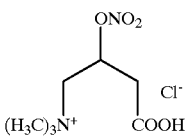
(XII)

of the formula (XIII),

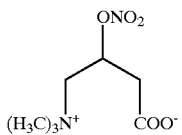
(XIII)

and of the formula (XIV),

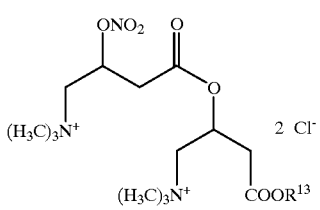
(XIV)

in which $R^{13}$ represents H or a $C_1$ to $C_6$ alkyl group are particularly preferred.

Compounds of the formula (XV) in particular contribute to achieving the object of the invention, $$(HOCH_2)_q(O_2NOCH_2)_rC(CH_2OR^{14})_s \qquad (XV)$$

in which $R^{14}$ represents the acyl group from a compound of the formula (X) to (XIV), in which $R^{11}$ also may represent H, a $C_1$ to $C_6$ alkanoyl group, salicyloyl or acetylsalicyloyl or $-CO-CH_2-CH(OH)-CH_2-NR^8R^9$, and q to s are integers, and: $q+r+s=4$ and r and s are $\geq 1$, in particular compounds of the formula (XVI), (XVI)

and those of the formula (XVII), (XVII)

Depending on the conditions of reaction and the starting materials, the end product is obtained either as a free acid or base, as a basic or acid addition salt or a betaine, each of which lie within the scope of the invention. Thus, acidic, basic, neutral or mixed salts and hydrates may be obtained. On the one hand, each of the salts may be converted into the free acid or base by using corresponding agents or by ion-exchange in a manner known per se. On the other hand, the free acids or bases obtained may form salts with organic or inorganic bases or acids. When preparing base addition salts, bases are used in particular which form suitable therapeutically acceptable salts.

These bases are for example hydroxides or hydrides of the alkali and alkaline-earth metals, ammonia and amines. When preparing acid addition salts, those acids are preferably used which form suitable therapeutically acceptable salts. These types of acids are for example, hydrohalic, sulfonic, phosphoric, nitric and perchloric acids, furthermore aliphatic, acyclic, aromatic, heterocyclic carboxylic or sulfonic acids such as formic, acetic, propionic, succinic, glycolic, lactic, malic, tartaric, citric, gluconic, sugar, glucuronic, ascorbic, maleic, hydroxymaleic, pyruvic, phenylacetic, benzoic, p-aminobenzoic, anthranilic, p-hydroxybenzoic, salicylic, acetylsalicylic, p-aminosalicylic, embonic, methanesulfonic, ethanesulfonic, hydroxyethanesulfonic, ethylenesulfonic, halobenzenesulfonic, toluenesulfonic, naphthylsulfonic or sulfanilic acids and amino acids such as for example methionine, tryptophane, lysine or arginine. These and other salts of the new compound (sic) may be used as agents for purifying the free acids or bases which are obtained. Salts of the acids or bases may be produced and isolated from solutions, and then the free acid or base may be recovered from a fresh salt solution in a purer condition. As a result of the relationship between the new compounds in their free form and as their salts, these salts also lie within the scope of the invention. Some of the new compounds may be present as optical isomers or racemates, depending on the choice of starting materials and the method used, or if they contain at least two asymmetric carbon atoms they may also be present as an isomeric mixture (racemate mixture). The isomeric mixture obtained (racemate mixture) may be separated into pure racemates with the assistance of chromatography or fractional crystallisation to give two stereoisomers (diastereomers). The racemates obtained may be separated using methods known per se, such as by recrystallising from an optically active solvent, by using microorganisms, by reacting with optically active agents to produce compounds which can be separated or by separating on the basis of the different solubilities of the diastereoisomers. Suitable optically active agents are the L- and D-forms of tartaric, di-o-toluyltartaric, malic, mandelic, gluconic, sugar, glucuronic, camphorsulfonic, quinine or binaphthylphosphoric acids. The more active portion of the two mirror image isomers is preferably isolated. The starting materials are known or, if they are intended to be new, can be obtained by methods known per se. At the same time the use of pharmacologically acceptable derivatives of all the previously mentioned compounds is possible. In particular, useful addition compounds, salts or enzymatically or hydrolytically decomposable compounds such as esters, amides, hydrazides, which are obtained e.g. by N-amination (DD-B1-230 865 and DD-A3-240 818) of the corresponding amino compounds, hydrazinium salts and similar represent, if not mentioned above, possible variations.

Compounds according to the invention may be used clinically as such or as part of a pharmaceutical preparation, as an individual active substance in combination with each other or with known heart/circulation or vascular treatments, for example combined with ACE inhibitors, antiarteriosclerotic agents, antihypertensive agents, beta-blockers, cholesterol reducers, diuretics, calcium antagonists, coronary dilators, lipid reducers, peripheral vasodilators, phosphodiesterases, in particular —(V)—, or thrombocyte aggregation inhibitors or other substances also used as treatment for heart/circulation conditions. The provision of pharmaceutical preparations is performed using methods and rules which are generally familiar to a person skilled in the pharmaceutical field wherein the choice of technology to be used and the galenic auxiliary agents to be used are governed in the first instance by the active substance being processed. Here matters relating to its chemico-physical properties, the form of application selected, the duration of activity required, the location of action and avoidance of medicament/auxiliary substance incompatibilities are of particular importance. The person skilled in the art therefore has to select the form of medicament, the auxiliary agents and the method of preparation using known substance and process parameters in a manner which is trivial per se. The relevant form of medicament should be designed in such a way that it contains the particular active substance in an amount which produces therapeutic levels in the plasma and enables the daily dose to be divided into one to two units for controlled release systems and into up to ten individual doses in other types of medicament. Continuous application using long term infusion is also suitable. To produce endothelial protective effects, long lasting therapeutic levels in the blood are generally striven for. According to the invention the compounds mentioned may be applied in particular orally, intravenously, parenterally, sublingually or transdermally. The particular medicament preparation is preferably provided in liquid or solid form. Solutions, in particular for the preparation of drops, injections or aerosol sprays, furthermore suspensions, emulsions, syrups, tablets, film-coated tablets, dragees, capsules, pellets, powders, pastilles, implants, suppositories, creams, gels, salves, patches or other transdermal systems are suitable for this purpose. The pharmaceutical preparations contain conventional galenic organic or inorganic supports and auxiliary substances which should themselves be chemically inert towards the particular active substances. Chemical derivatisation during application to support materials is also included. This applies in particular to the production of adducts with sugar derivatives such as croscarmeloses or cyclodextrins. Suitable pharmaceutical auxiliary substances are, without being restricted thereto, water, salt solutions, alcohols, plant oils, polyethylene glycols, gelatines, lactoses, amyloses, magnesium stearate, talcum, highly dispersed silicon dioxide, paraffin, fatty acid mono- and diglycerides, cellulose derivatives, polyvinylpyrrolidone and the like. The preparation may be sterilised and if required may have added thereto auxiliary substances such as fillers, binders, lubricants, mould release agents, intestinal lubricants, decomposing agents, moisture retainers, adsorption agents or antidisintegrants, preservatives, stabilisers, emulsifiers, solvent promoters, salt to alter the osmotic pressure, buffer solutions, dyes, fragrances, flavourings or sweeteners. A person skilled in the pharmaceutical art is able to avoid medicament/auxiliary agent incompatibilities by basing his choice on the relevant substance parameters.

Surprisingly, it was found that compounds according to the invention have the required properties. In addition they are characterised by an optimised NO liberation, e.g. due to their differentiated concentration of reductive biotransforming NO precursor groups or an improved multi-phase NO liberation and, depending on the ultimate application, increased lipophilicity or hydrophilicity and also by lowering the pharmacodynamic threshold, reduced endothelial increase in the plasma, pronounced thrombocyte aggregation inhibition by thrombocyte-active groups and, even in sub-haemodynamic dosage, by endothelial-protective effects. Particularly advantageous is the fact that compounds according to the invention are characterised by good penetration of physiological membranes. Furthermore it was found that in particular the compounds derived from carboxyl compounds and their salts or quaternary ammonium compounds can be processed to give pharmaceutical preparations in the form of sprays and injection solutions. Compounds used in accordance with the invention, surprisingly, show in functional tests on isolated blood vessels (rabbit aorta) a high vaso-dilatory property with improved bioavailability and increased hydrophilicity as well as facilitated biotransformation to give the final metabolites, wherein these final metabolites are generally very well tolerated or are compounds which are normally present in the body. They are characterised, surprisingly, as strongly hydrophilic, nitrate vasodilators which have a long half-life and improved bioavailability as compared with lipophilic nitrates. It was surprising that compounds according to the invention could on the one hand trigger the strong pharmacodynamic effects which are typical of lipophilic organic nitrates without their pronounced short term effect and on the other hand have the characteristic long term effect of more hydrophilic organic nitrates, that is they combine the advantages of lipophilic and hydrophilic organic nitrates within the compounds used without exhibiting any of their pharmacodynamic disadvantages. Thus using the invention described, improved and considerably extended therapeutic opportunities are opened up and pathological conditions such as heart and circulatory illnesses, in particular coronary heart disease, vascular stenoses and bleeding problems in the peripheral arteries, hypertonia, micro and macroangiopathies within the context of diabetes mellitus, arteriosclerosis and the secondary illnesses resulting therefrom, furthermore erectile disfunction, elevated internal eye pressure, uterine spasms, menopausal problems, etc. can be treated. Some of the compounds described above may be characterised, on the basis of their chemico-physical properties, as explosives, which may also enable their use as such. A person skilled in the art is able to select compounds for this purpose on the basis of known test processes. In contrast to that, however, a number of substances according to the invention do not have this property or this property is only weakly expressed so that these compounds are characterised by the absence of the disintegrant properties which are typical of organic nitrates while at the same time being characterised by the retention of and improvement in pharmacological effects due to a particularly simple and reliable method of preparation, handling and further processing. In addition compounds described in the present invention are useful starting compounds and intermediates for the preparation of chemical derivatives which may themselves be used as pharmaceutical active substances. The examples given below are intended to explain the invention in more detail without however restricting its scope.

EXAMPLES

Example 1

158 g (0.5 mol) of pentaerythrityl tetranitrate (PETN) were dissolved in a mixture of 300 ml of dioxan and 300 ml of ethanol at boiling point and different amounts of aqueous hydrazine hydrate solution (1.5–4 mol) were added thereto in portions over the course of 1 hour. Then the reaction mixture was boiled under reflux for a further 2.5 hours. Nitrogen, ammonia and nitrogen oxides evolved during the reaction. After reaction, the solvent was evaporated off at 15 mm Hg and the residue, if required, was shaken up several times with 100 ml portions of water until the volume of the oil layer could no longer be reduced during shaking. The aqueous extracts (A) were combined and the remaining oily layer was dissolved in twice the volume of ethanol. The white precipitate of PETN, which may have settled out, was filtered off after 24 hours: it had a m.p. of 132° C. After recrystallising twice from acetone its m.p. had increased to 141° C. Ethanol was evaporated from the filtrate at 15 mm Hg. The viscous, oily residue consisted of pentaerythrityl trinitrate (PETriN).

Example 2

The combined aqueous extracts A were shaken up 3 times with ether and the ether was evaporated out of the etheral layer isolated from the aqueous layer B after drying over anhydrous $Na_2SO_4$. The very viscous, oily residue after evaporation was identified as crude pentaerythrityl dinitrate (PEDN). The aqueous fraction B which, in addition to pentaerythrityl mononitrate (PEMN) and pentaerythrityl denitration products, contained mainly hydrazine nitrite, was acidified successively with 2N $H_2SO_4$ until the production of gas could be heard ($N_2$, $N_2O$, NO, $N_3H$), then concentrated by evaporation at 20 mm Hg until the separation of a solid product started to occur and then the ether was removed. The crystalline substance with a m.p. of 62° C. which remained after evaporation of the ether was identified as crude PEMN. After washing with cold chloroform and recrystallising from chloroform the platelets obtained had a m.p. of 79° C. The extraction residue was evaporated to dryness at 10 mm Hg and the residue was stirred into a small amount of water. The white crystals which were filtered off, and which had a m.p. of 260° C. after recrystallisation from the same amount by weight of water, were identified as pure pentaerythritol.

Example 3

In order to purify the crude substances PETriN and PEDN, these were converted into the relevant acetates and alcoholised to give the pure products after recrystallisation from ethanol. To 135.5 g (0.5 mol) of crude PETriN [or 56.5 g (0.25 mol) of PEDN] a mixture of 50 ml of acetic anhydride and 20 ml of acetyl chloride were added in portions with cooling and stirring. The mixture which solidified after reaction was stirred into 50 ml of ethanol and separated under suction twice. The colourless crystals of pentaerythrityl trinitrate acetate (PETriNAc) with a m.p. of 85 to 86° C. had a m.p. of 89° C. after recrystallising twice from ethanol. The yield of pure product was 121 g (77%). Pentaerythrityl dinitrate diacetate (PEDNAc) also formed colourless crystals with a m.p. of 42 to 43° C. which increased to 47° C. after recrystallisation twice from ethanol. The yield of pure product was 56 g (72%). 104.4 g (0.3 mol) of PETriNAc or 51.7 g (0.15 mol) of PEDNAc were dissolved in 400 ml of hot ethanol, a solution of 1.5 g of NaOH in 50 ml of ethanol was added and the azeotropic mixture of ethanol/ethyl acetate ($K_p$ 71.8° C./760 mm) was distilled off. After completion of ethyl acetate formation, a further 1.5 g of NaOH and 50 ml of ethanol were added and again fractionated until further ethyl acetate no longer passed over. Then the ethanol was evaporated off at 15 mm Hg and the residue in the case of the substance PETriN, was shaken up 3 times with 20 ml of water and in the case of the substance PEDN was stirred into 100 ml of water and ether removed 3 times. After drying under vacuum or removing the ether respectively, the pure substances PETriN and PEDN were obtained as colourless viscous liquids, which were dried under vacuum over $P_2O_5$ for analysis.

Example 4

PETriN was also processed in such a way that it was stirred into 100 ml of water after washing with water and then allowed to stand until the next day at a temperature which was no higher than 20° C. Colourless crystals were obtained, stable in air, with a m.p. of 32° C., containing 2.14±0.05% of water according to the Karl-Fischer reaction and 2.15% of water according to vacuum drying, corresponding to a hydrate with the composition $C_5H_9O_{10}N_3.1/3H_2O$.

Example 5

PETriN is prepared by nitration of pentaerythritol with $HNO_3$ (95% strength) in the presence of urea.

Example 6

PEDN and PEMN are prepared from PETriN by hyrazinolysis (4 mol $NH_2NH_2$ (50% strength)) with subsequent column chromatographic separation of the 1:1 mixture.

Example 7

0.0074 mol of $KMnO_4$ is added in portions with vigorous stirring to a solution of 0.0037 mol of pentaeythrityl trinitrate (PETriN), 5.5 ml of benzene, 9 ml of water and 0.15 ml of Aliquate® 336. When addition is complete, the temperature is held at 15° C. for 2 hours. Then aqueous hydrogen sulfite solution is added to the mixture, the mixture is acidified with $H_2SO_4$ and the benzene layer is isolated. After removing the solvent, 3-nitryloxy-2,2-bis(nitryloxymethyl) propionic acid (Tri-PA) is obtained as a solid residue which is recrystallised several times from methylene chloride (yield: 72%).

Example 8

1.0 g (0.0061 mol) of 2,2-bis(hydroxymethyl)malonic acid is added to a mixture of 2.5 g of 95 (%) strength $HNO_3$, a spatula tip-full of urea and 10 ml of water, with stirring and ice-cooling. After 10 min 2.5 g of 94% strength $H_2SO_4$ are added dropwise and the mixture is stirred for another hour at 0° C. The organic layer is separated and evaporated down. 2,2-bis(nitryloxymethyl)malonic acid is obtained as a viscous oil as the residue, which is purified column chromatographically.

Yield: 45%. Elemental analysis: (C: corresponds, H: corresponds, N: corresponds).

Example 9

2-carboxy-2-nitryloxymethylmalonic acid

To a mixture cooled to 0° C. of 2.5 g of 95 (%) strength $HNO_3$, a spatula-full of urea and 10 ml of water is added with stirring and ice-cooling, 1.0 g (0.004 mol) of carboxy-2-hydroxymethylmalonic acid. After 10 min 2.5 g of 94% strength $H_2SO_4$ are added dropwise with stirring and stirring is continued for another hour at 0° C. The organic layer is isolated and evaporated down. 2-carboxy-2-nitryloxymethylmalonic acid is obtained as the residue as a viscous oil which is purified column chromatographically.

Yield: 30%. Elemental analysis: (C: corresponds, H: corresponds, N: corresponds).

Example 10

0.001 mol of bis-MA is azeotropically esterified with 0.0011 mol of 4-butyl-3-hydroxy-1,2,4-oxydiazole-5-one in the presence of benzene and catalytic amounts of $H_2SO_4$ (yield: 60%).

Example 11

0.001 mol of bis-MA is azeotropically esterified with 0.0011 mol of 4-(2-phenylethyl)-3-hydroxyl-1,2,4-oxadiazole-5-one in the presence of benzene and catalytic amounts of $H_2SO_4$ (yield: 53%).

Example 12

0.001 mol of CN-MA is azeotropically esterified with 0.0022 mol of 4-butyl-3-hydroxyl-1,2,4-oxadiazole-5-one in the presence of benzene and catalytic amounts of $H_2SO_4$ (yield: 45%).

Example 13

0.01 mol of 4-chloro-3-hydroxybutanoic acid is converted into 4-chloro-3-nitroxybutanoic acid with 3 times the amount of $HNO_3/H_2SO_4$ (nitrating acid) (yield: 76%).

Example 14

Aqueous trimethylamine solution is added to 0.005 mol of 4-chloro-3-nitroxybutanoic acid in a sealable vessel, the vessel is sealed and the resulting mixture is heated at 80° C. for 1 hour. After cooling, the solution is evaporated down, cooled and the mixture left to crystallise with cooling. 3-nitryloxy-4-trimethylammoniumbutyryl chloride (salt) is obtained (yield: 71%).

Example 15

0.001 mol of the compound according to example 14 are azeotropically esterified with 0.0011 mol of PETriN in the presence of benzene and catalytic amounts of $H_2SO_4$ (yield: 37%).

Example 16 a) 3-Nitryloxy-2,2-bis(nitryloxymethyl)propionyl chloride 1 g (3.5 mmol) of Tri-PA is heated with 5.3 mmol of thionyl chloride for 1.5 hours under reflux: the excess thionyl chloride is distilled off, first on a water bath and then under vacuum. The residue is taken up in diethylether and washed rapidly with a little ice-water. The organic phase is isolated, dried over sodium sulfate and the solvent is evaporated under vacuum. The oily 3-nitryloxy-2,2-bis (nitryloxymethyl)propionyl chloride (tri-PACl) produced is pure enough for use in further reactions. Yield: 75%.

b) 2,2-bis(nitryloxymethyl)malonyl chloride and 2-chlorocarbonyl-2-nitryloxymethylmalonyl dichloride The acid chlorides of the compounds 2,2-bis (nitryloxymethyl)malonic acid (bis-MA) and 2-carboxy-2-nitryloxymethylmalonic acid (CN-MA) are obtained in the same way. To prepare 2,2-bis(nitryloxymethyl)malonyl dichloride (bis-MACl), double the amount of thionyl chloride is used and to prepare 2-chlorocarbonyl-2-nitryloxymethylmalonyl dichloride (CN-MACl), 3 times the amount of thionyl chloride is used. Yield: 70 and 45% respectively.

c) Methyl 3-nitryloxy-2,2-bis(nitryloxymethyl) propionate 1 ml of thionyl chloride and 1 drop of dry DMF are added to 7 mmol of tri-PA and stirred with the exclusion of moisture for 20 min at room temperature. Then excess thionyl chloride is distilled off and 10 ml of dry methanol is added to the reaction mixture cooled to 0° C. After 30 min the mixture is diluted with 30 ml of water and extracted 5 times with diethylether. Column chromatographic purification (hexane: ethyl acetate=2:1) of the crude product obtained after evaporating off the solvent produced methyl 3-nitryloxy-2,2-bis(nitryloxymethyl)propionate as colourless crystals. Yield: 44%.

$C_6H_9N_3O_{11}$, M=299.14; m.p.=66° C.; $R_f$=0.65 (silica gel, hexane: ethyl acetate=1:1).

d) Ethyl 3-nitryloxy-2,2-bis(nitryloxymethyl)propionate 10.5 mmol of ethanol, 20 mg of toluenesulfonic acid and 30 ml of chloroform are added to 1 g (3.5 mmol) of tri-PA and heated for 12 hours on a water separator under reflux. The chloroform phase is washed with aqueous bicarbonate solution and with water, the solvent is evaporated off under vacuum and the residue is purified column chromatographically. Ethyl 3-nitryloxy-2,2-bis(nitryloxymethyl)propionate is obtained as colourless oil. Yield: 85%.

e) Butyl 3-Nitryloxy-2,2-bis(nitryloxymethyl)propionate 1 ml of n-butanol is dissolved in 5 ml of pyridine and 0.5 g (1.7 mmol) of tri-PACl dissolved in 5 ml of tetrahydrofuran is added thereto with ice-cooling. The mixture is heated for 1 hour on a water bath. The mixture is then poured into 50 ml of ice-water and carefully neutralised with hydrochloric acid. The oily ester which separates out is taken up in diethylether, washed with aqueous sodium carbonate solution and water, the organic phase is dried over sodium sulfate and the solvent is evaporated off under vacuum. Column chromatographic purification of the residue produces butyl 3-nitryloxy-2,2-bis(nitryloxymethyl)propionate as a colourless oil. Yield: 69%.

f) The esters of the carboxylic acids bis-MA and CN-MA are obtained in the same way by doubling (in the case of bis-MA) and tripling (in the case of CN-MA) respectively the amount of reagent added.

g) Diethyl 2,2-bis(nitryloxymethyl)malonate 0.015 mol of diethyl 2,2-bis(hydroxymethyl)malonate are slowly added to a solution of 90 g of degassed 100% nitric acid at −5° C. under a stream of air. The reaction mixture is thoroughly ventilated for a further 120 min at −5° C. and then poured into ice-water. The aqueous phase is de-etherified twice, the organic phase is washed with 10% strength hydrogen carbonate solution and with water, dried over sodium sulfate and the solvent evaporated off under vacuum. The residue is separated on a chromatography column. Yield: 94%. $R_f$=0.52 (silica gel, hexane: ethyl acetate=2:1); $^1H$ NMR (300 MHz, CDCl$_3$): corresponds; $^{13}C$ NMR (75 MHz, CDCl$_3$): corresponds.

h) 3-nitryloxy-2,2-bis(nitryloxymethyl)propionamide 1 g (3.4 mmol) of tri-PACl is dissolved in 25 ml of dioxan and excess concentrated ammonia solution is added thereto. After 30 min the mixture is poured into 100 ml of ice-water and slightly acidified with dilute hydrochloric acid. The oily 2,2-bis(nitryloxymethyl)-3-nitryloxypropionamide which separates out is purified column chromatographically. Yield: 65%.

i) 3-nitryloxy-2,2-bis(nitryloxymethyl)propionamide 1 ml of thionyl chloride and 1 drop of dry DMF are added to 7 mmol of tri-PA and the mixture is stirred with the exclusion of moisture for 20 min at room temperature. Then 3 ml of cold concentrated NH$_3$ solution are added to the reaction mixture and the solution is allowed to cool to room temperature. After extracting the aqueous phase with diethyl ether 5 times and removing the solvent, an oily crude product is obtained from which 3-nitryloxy-2,2-bis(nitryloxymethyl)propionamide is isolated as colourless crystals by means of column chromatography (hexane:ethyl acetate=1:1). Yield: 32%; $C_5H_8N_4O_{10}$, M=284.13; $R_f$=0.52 (silica gel, hexane:ethyl acetate=1:1). m.p. 71–72° C. (CHCl$_3$).

j) 3-nitryloxy-2,2-bis(nitryloxymethyl)propionic acid N-benzylamide 1 g (3.5 mmol) of methyl 3-nitryloxy-2,2-bis(nitryloxymethyl)propionate is heated with 3 ml of benzylamine and 100 ml of ammonium chloride for 3 hours at 130° C., cooled, taken up in 50 ml of chloroform and washed in sequence with water, dilute hydrochloric acid, aqueous bicarbonate solution and again with water. The crude product obtained after evaporating off the solvent is purified column chromatographically. 3-nitryloxy-2,2-bis(nitryloxymethyl)propionic acid N-benzylamide is obtained as a colourless oil. Yield: 73%.

k) 3-nitryloxy-2,2-bis(nitryloxymethyl)propionic acid hydrazide 1 g (3.5 mmol) of methyl 2,2-bis(nitryloxymethyl)-3-nitryloxypropionate is heated with excess aqueous hydrazine hydrochloride solution for 5 hours on a water bath. The mixture is poured onto ice and slightly acidified with hydrochloric acid. After column chromatographic separation of the oil which is produced, 3-nitryloxy-2,2-bis(nitryloxymethyl)propionic acid hydrazide is obtained as a colourless oil. Yield: 63%.

l) The amides or hydrazides of the carboxylic acids bis-MA and CN-MA are produced in the same way by doubling and tripling respectively the reagents.

The compounds described above under a) to 1) may be used as starting materials and intermediates for further reactions.

Example 17

3.4 mmol of L-carnitine hydrochloride are esterified with 1 g (3.4 mmol) of tri-PACl in 25 ml of dioxan. After 30 min, the mixture is poured into 100 ml of ice-water and slightly acidified with dilute hydrochloric acid. The oily product which separates out is purified column chromatographically. Yield: 40%.

Example 18

3-trimethylammonium-2-nitryloxypropanecarboxylate 1 g of carnitine hydrochloride is added to 8 ml of 70% strength nitric acid cooled to 0° C. After adding 5.5 ml of 96% strength sulfuric acid at 0° C., the mixture is stirred at room temperature for 1 hour and poured onto 50 ml of ice-water. After neutralisation (pH 7.0) with 10% strength caustic soda solution, the mixture is evaporated to dryness under vacuum, the residue is extracted twice with ethanol, the alcohol is evaporated off and the crude product obtained is purified column chromatographically (silica gel, methanol) (yellowy oil). Yield 56%.

Example 19

Testing the pharmacological effect of the compounds:
a) The test is performed with cultivated cells (RFL-6-fibroplasts, LLC-PK1-epithelial cells), which are known as a model for characterising the activity and tolerance profiles of NO donors (Bennet et al., J. Pharmacol. Ther. 250 (1989), 316; Schröder et al., J. Appl. Cardiol. 2 (1987), 301; J. Pharmacol. Exp. Ther. 245 (1988), 413; Naunyn Schmiedeberg's Arch. Pharimacol. 342 (199), 616; J. Pharmacol. Exp. Ther. 262 (1992), 298; Adv. Drug. Res., 28 (1996), 253). The intracellular accumulation of cGMP as a parameter for nitrate effect and bioactivation is measured using a radio-immuno assay.
b) The thrombocyte aggregation and thrombus production inhibiting effect of the compounds is determined using Rehse et al.'s method (Arch. Pharm. 324, 301–305 (1991); Arch. Pharm. Pharm. Med. Chem. 329, 535 (1996)), which is established as a model for describing anticoagulant and antithrombotic properties.
c) The endothelial protective effect of the compounds is determined using Noack and Kojda's known method (DE-A1-44 10 997).
d) The vasodilating properties were tested in experiments on isolated aortal rings from rabbits (Hüsgen, Noack, Kojda: Int Confer. "Mediators in the cardiovascular system", p.9, Malta 2–5.6.1994), by suspending these in organ baths and stimulating them with vasoconstrictors such as phenylephrin. After establishing a stable, smooth muscular tone, the effect of the tone is determined by cumulative concentration/effect curves for the vasodilators mentioned above. For this, increasing concentrations of between 1 nM and 10 μM of the vasodilator are added to the organ bath buffer, wherein the system is not washed out between the various fractions. As a result of adding the substances, there was a stepwise increase in the contraction in the presence of the vasoconstrictor in all the aorta rings. The extent of relaxation is expressed as a percentage of the contraction still remaining (residual contraction) for the particular active substance concentration. The half peak active concentration EC50 gives the strength of activity and is determined as the pD2 value (concentration in logM).

Example 20

A tablet had the composition:

| Active substance(s) | | x mg |
|---|---|---|
| Lactose | DAB 10 | 137 mg |
| Potato starch | DAB 10 | 80 mg |
| Gelatine | DAB 10 | 3 mg |
| Talcum | DAB 10 | 22 mg |
| Magnesium stearate | DAB 10 | 5 mg |
| Silicon dioxide, highly dispersed | DAB 10 | 6 mg |
| Active substance(s): | | |
| a) Compound according to example 10 | | 20 mg |
| b) Compound according to example 10 | | 50 mg |
| c) Compound according to example 10 | | 80 mg |
| d) Compound according to example 11 | | 20 mg |
| e) Compound according to example 11 | | 50 mg |
| f) Compound according to example 11 | | 80 mg |
| g) Compound according to example 12 | | 20 mg |
| h) Compound according to example 12 | | 50 mg |
| i) Compound according to example 12 | | 80 mg |
| j) Compound according to example 14 | | 20 mg |
| k) Compound according to example 14 | | 50 mg |
| l) Compound according to example 14 | | 80 mg |
| m) Compound according to example 15 | | 20 mg |
| n) Compound according to example 15 | | 50 mg |
| o) Compound according to example 15 | | 80 mg |
| p) Compound according to example 17 | | 50 mg |
| q) Compound according to example 7 | | 30 mg |
| Compound according to example 14 | | 50 mg |
| r) Compound according to example 7 | | 30 mg |
| Compound according to example 15 | | 50 mg |
| s) Compound according to example 14 | | 30 mg |
| Pentaerythrityl tetranitrate | | 50 mg |
| t) Compound according to example 15 | | 30 mg |
| Pentaerythrityl tetranitrate | | 50 mg |
| u) Compound according to example 10 | | 50 mg |
| Acetylsalicylic acid | | 50 mg |
| v) Compound according to example 12 | | 50 mg |
| Acetylsalicylic acid | | 50 mg |
| w) Compound according to example 14 | | 50 mg |
| Acetylsalicylic acid | | 50 mg |
| x) Compound according to example 15 | | 50 mg |
| Acetylsalicylic acid | | 50 mg |
| y) Compound according to example 14 | | 50 mg |
| Captopril | | 25 mg |
| z) Compound according to example 15 | | 50 mg |
| Captopril | | 25 mg |

What is claimed is:

1. A compound having a formula (I)

$$(O_2NOCH_2)_m C(CH_2OH)_n (CH_2COR^1)_o (COR^1)_p \qquad (I)$$

in which $R^1$ represents a group of formula (II),

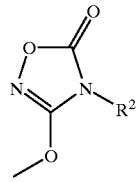

(II)

$R^2$ represents a $C_1$ to $C_{20}$ alkyl group, benzyl, cyclohexylmethyl, 4-chlorobenzyl, 4-nitrobenzyl, 2-phenylethyl, 3-phenylpropyl, 3-cyclohexylpropyl, 3-phthalimidylpropyl, 1-naphthylmethyl, cinnamyl, 5-ethoxy-carbonylbutyl, 3-aminopropyl, —(CH$_2$)$_3$CH (NHCOCH$_3$)COOH, —(CH$_2$)$_3$CH (NHCOCH$_3$) COOCH$_3$, or 1,6-hexane-bis-, and m to p are integers, and $$m+n+o+p=4,\ m \geq 1,\ o \text{ and/or } p \geq 1,$$

and their therapeutically acceptable salts.

2. A compound having a formula (III), $$(O_2NOCH_2)_m C(CH_2OH)_n (CH_2COR^3)_o (COR^3)_p \qquad (III)$$

in which $R^3$ represents a group of formula (IV)

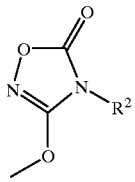

(IV)

$R^2$ represents a $C_1$ to $C_{20}$ alkyl group, benzyl, cyclohexylmethyl, 4-chlorobenzyl, 4-nitrobenzyl, 2-phenylethyl, 3-phenylpropyl, 3-cyclohexylpropyl, 3-phthalimidylpropyl, 1-naphthylmethyl, cinnamyl, 5-ethoxy-carbonylbutyl, 3-aminopropyl, —$(CH_2)_3$CH$(NHCOCH_3)$COOH, —$(CH_2)_3$CH$(NHCOCH_3)$COOCH$_3$, or 1,6-hexane-bis-, and m to p are integers, and $m+n+o+p=4$, $m \geq 1$, o and/or $p \geq 1$, and their therapeutically acceptable salts.

3. A compound having a formula (VI),

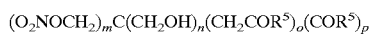

(VI)

in which $R^5$ is (2-carboxyphenyl)oxy or (2alkoxycarbonyl-phenyl)oxy and m to p are integers, and $m+n+o+p=4$, $m \geq 1$, o and/or $p \geq 1$, and their therapeutically acceptable salts.

4. A compound having a formula (VIII),

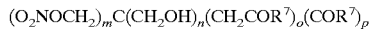

(VIII)

in which $R^7$ is a group of formula (IX),

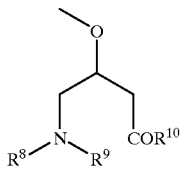

(IX)

$R^8$ and $R^9$, independently, represent a $C_1$ to $C_6$ alkyl group or together represent a $C_1$ to $C_6$ alkylene group, $R^{10}$ represents OH, NHR$^8$R$^9$, a $C_1$ to $C_6$ alkoxy group, (2-carboxyphenyl)oxy, (2-alkoxycarbonylphenyl)oxy, (1-carboxymethyl-2-dialkylamino)ethoxy, (1-carboxymethyl-2-trialkylammonium)ethoxy, (1-alkoxycarbonylmethyl-2-dialkylamino)ethoxy, (1-alkoxycarbonylmethyl-2-trialkylammonium) ethoxy, and m to p are integers and $m+n+o+p=4$, $m \geq 1$, o and/or $p \geq 1$, and their therapeutically acceptable salts, quaternary salts, or betaines.

5. A pharmaceutical agent containing one or more compounds of claim 1, 2, 3, or 4.

6. A pharmaceutical agent according to claim 5 further comprising other active agents for treating heart/circulation or vascular illnesses selected from the group consisting of ACE inhibitors, antiartheriosclerotic agents, antihypertensive agents, beta-blockers, cholesterol reducers, diuretics, calcium antagonists, coronary dilators, lipid reducers, peripheral vasodilators, phosphodiesterase inhibitors, and thrombocyte aggregation inhibitors.

7. The compound of claim 1 wherein the $C_1$ to $C_{20}$ alkyl group is selected from the group consisting of methyl, ethyl, n-propyl, i-propyl, n-butyl, n-pentyl, n-hexyl, and n-octyl.

8. The compound of claim 2 wherein the $C_1$ to $C_{20}$ alkyl group is selected from the group consisting of methyl, ethyl, n-propyl, i-propyl, n-butyl, n-pentyl, n-hexyl, and n-octyl.

* * * * *